(12) United States Patent
Zhang et al.

(10) Patent No.: US 9,724,057 B2
(45) Date of Patent: Aug. 8, 2017

(54) MAGNETIC FIELD ACTUATION OF DETECTORS IN A COMPUTED TOMOGRAPHY SCANNER

(71) Applicant: TOSHIBA MEDICAL SYSTEMS CORPORATION, Otawara-shi (JP)

(72) Inventors: Yuexing Zhang, Naperville, IL (US); Les Kvien, Mundelein, IL (US); Barry Roberts, Gurnee, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 149 days.

(21) Appl. No.: 14/788,238

(22) Filed: Jun. 30, 2015

(65) Prior Publication Data

US 2017/0000437 A1    Jan. 5, 2017

(51) Int. Cl.
| | | |
|---|---|---|
| *A61B 6/00* | (2006.01) | |
| *A61B 6/03* | (2006.01) | |
| *G01T 1/16* | (2006.01) | |
| *G01T 1/29* | (2006.01) | |

(52) U.S. Cl.
CPC ............ *A61B 6/4452* (2013.01); *A61B 6/032* (2013.01); *A61B 6/035* (2013.01); *A61B 6/4241* (2013.01); *A61B 6/4266* (2013.01); *A61B 6/4429* (2013.01); *G01T 1/1603* (2013.01); *G01T 1/2985* (2013.01); *A61B 6/447* (2013.01); *A61B 6/4435* (2013.01); *A61B 6/482* (2013.01)

(58) Field of Classification Search
CPC ..... A61B 6/035; A61B 6/4429; A61B 6/4452; A61B 6/4241
See application file for complete search history.

(56) References Cited

U.S. PATENT DOCUMENTS

| 4,137,455 A | 1/1979 | Fetter | |
|---|---|---|---|
| 7,453,977 B2 * | 11/2008 | DiBianca | ............... A61B 6/032 |
| | | | 257/E27.14 |
| 2014/0314196 A1 * | 10/2014 | Zou | ........ A61B 6/032 |
| | | | 378/4 |
| 2015/0146844 A1 | 5/2015 | Zamyatin et al. | |

(Continued)

FOREIGN PATENT DOCUMENTS

JP    2015-104664 A    6/2015

*Primary Examiner* — David E Smith
*Assistant Examiner* — James Choi
(74) *Attorney, Agent, or Firm* — Oblon, McClelland, Maier & Neustadt, L.L.P.

(57) ABSTRACT

A CT scanner apparatus includes an X-ray source mounted on a gantry of the CT scanner apparatus and configured to emit X-rays, and at least one magnetic field gradient circuit. The at least one magnetic field gradient circuit and the X-ray source rotate together. The CT scanner apparatus also includes a CT detector mounted on the gantry in fixed orbital opposition to the X-ray source. The CT detector is configured to detect the X-rays, wherein the CT detector and the X-ray source are configured to rotate along a first orbital path. The CT scanner apparatus also includes an array of fixed PCD assemblies arranged in a ring inside the first orbital path. Each PCD assembly is configured to rotatably actuate about a gantry support from a first position to a second position to reduce blockage of emitted X-rays when the magnetic field gradient circuit rotates within a predetermined distance of the PCD assembly.

8 Claims, 9 Drawing Sheets

(56) References Cited

U.S. PATENT DOCUMENTS

| | | | |
|---|---|---|---|
| 2015/0346354 A1* | 12/2015 | Arakita | G01T 1/1606 378/19 |
| 2016/0081641 A1* | 3/2016 | Bouhnik | G06T 7/97 378/5 |
| 2016/0146844 A1* | 5/2016 | Sabbadini | C07K 16/3076 435/7.94 |
| 2016/0213339 A1* | 7/2016 | Zhang | A61B 6/4241 |
| 2016/0217594 A1* | 7/2016 | Petschke | G06T 11/003 |

* cited by examiner

MAGNETIC FIELD ACTUATION OF DETECTORS IN A COMPUTED TOMOGRAPHY SCANNER

BACKGROUND

Field

The exemplary embodiments described herein relate to computed tomography (CT) systems. In particular, exemplary embodiments relate to a magnetic field actuation of X-ray detectors in a CT scanner.

Description of the Related Art

The X-ray beam in most computed tomography (CT) scanners is generally polychromatic. Yet third-generation CT scanners generate images based upon data according to the energy integration nature of the detectors. These conventional detectors are called energy-integrating detectors and acquire energy integration X-ray data. On the other hand, photon-counting detectors are configured to acquire the spectral nature of the X-ray source, rather than the energy integration nature. To obtain the spectral nature of the transmitted X-ray data, the photon-counting detectors split the X-ray beam into its component energies or spectrum bins and count the number of photons in each of the bins. The use of the spectral nature of the X-ray source in CT is often referred to as spectral CT. Since spectral CT involves the detection of transmitted X-rays at two or more energy levels, spectral CT generally includes dual-energy CT by definition.

Spectral CT is advantageous over conventional CT because spectral CT offers the additional clinical information included in the full spectrum of an X-ray beam. For example, spectral CT facilitates in discriminating tissues, differentiating between tissues containing calcium and tissues containing iodine, and enhancing the detection of smaller vessels. Among other advantages, spectral CT reduces beam-hardening artifacts, and increases accuracy in CT numbers independent of the type of scanner.

Conventional attempts include the use of integrating detectors in implementing spectral CT. One attempt includes dual sources and dual integrating detectors that are placed on the gantry at a predetermined angle with respect to each other for acquiring data as the gantry rotates around a patient. Another attempt includes the combination of a single source that performs kV-switching and a single energy-integrating detector, which is placed on the gantry for acquiring data as the gantry rotates around a patient. Yet another attempt includes a single source and dual energy-integrating detectors that are layered on the gantry for acquiring the data as the gantry rotates around a patient. All of these attempts at spectral CT were not completely successful in substantially solving issues, such as beam hardening, temporal resolution, noise, poor detector response, poor energy separation, etc., for reconstructing clinically viable images.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Embodiments herein describe magnetic field actuation of photon-counting detectors (PCDs) in a CT scanner. A magnetic field gradient-driven mechanism naturally synchronizes actuation of an interposer assembly module (IAM) of the PCD with X-ray source position. The synchronization is accomplished without motion control or synchronization electronics, and without mechanical contact between a rotating base and a stationary base.

In one embodiment, a CT scanner apparatus includes an X-ray source mounted on a gantry of the CT scanner apparatus and configured to emit X-rays, and at least one magnetic field gradient circuit. The at least one magnetic field gradient circuit and the X-ray source rotate together. The CT scanner apparatus also includes a CT detector mounted on the gantry in fixed orbital opposition to the X-ray source. The CT detector is configured to detect the X-rays, wherein the CT detector and the X-ray source are configured to rotate along a first orbital path. The CT scanner apparatus also includes an array of fixed PCD assemblies arranged in a ring inside the first orbital path. Each PCD assembly is configured to rotatably actuate about a gantry support from a first position to a second position to reduce blockage of emitted X-rays when the magnetic field gradient circuit rotates within a predetermined distance of the PCD assembly.

In one embodiment, a PCD assembly includes a PCD circuit, an IAM configured to directly face an orbital path of an orbiting X-ray source, and a paramagnetic material located at one end of the IAM. The PCD assembly also includes a spring mechanism located at a mid-section of the PCD assembly. The spring mechanism is configured to maintain a transverse position of the PCD assembly relative to an X-ray beam from the X-ray source during an absence of a magnetic field, and is configured to rotate the PCD assembly to a parallel position relative to the X-ray beam emitted from the X-ray source during a presence of the magnetic field.

Figure 1:
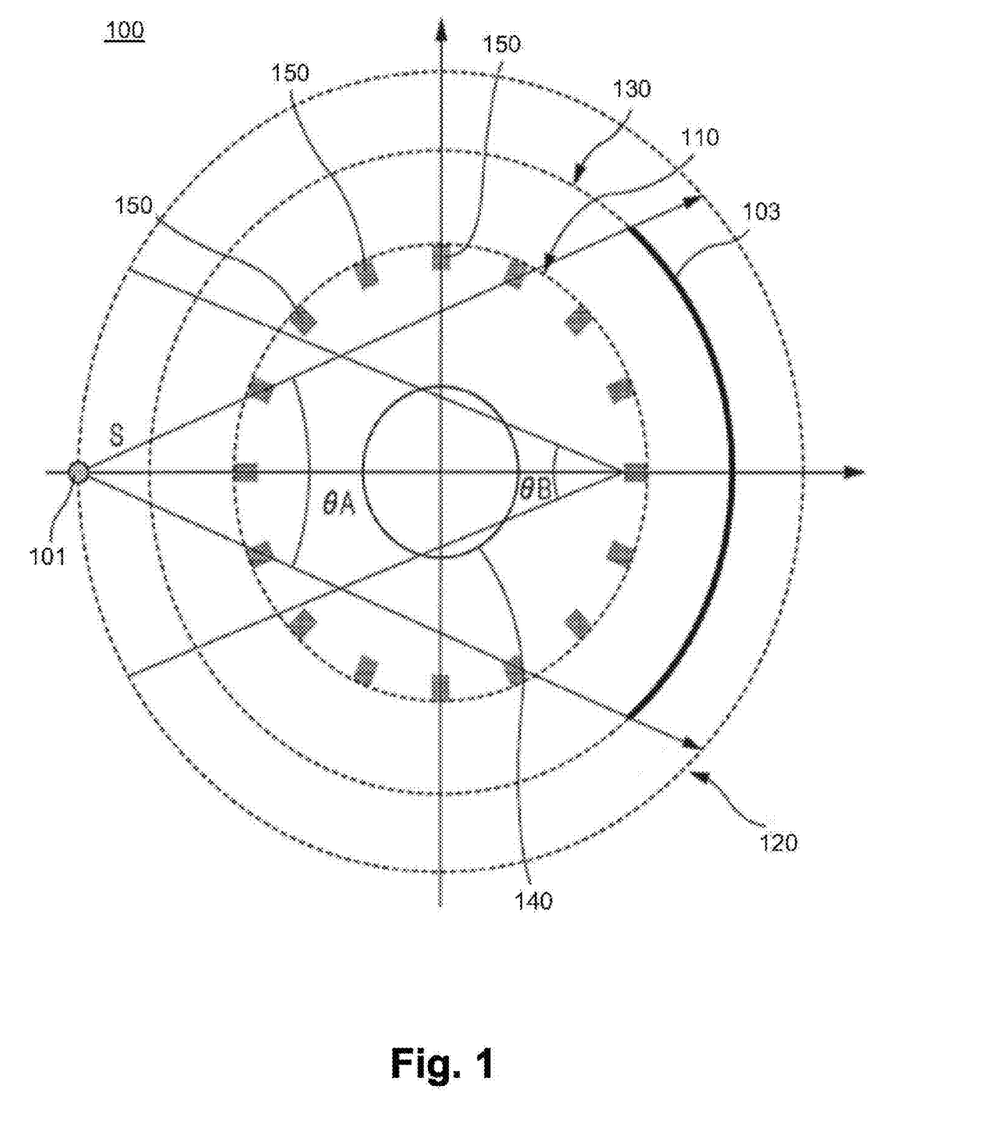
FIG. 1 is a cross-sectional diagram of a combined third-generation and fourth-generation computed tomography (CT) apparatus according to one embodiment.

Referring now to the drawings, wherein like reference numerals designate identical or corresponding parts throughout the several views, FIG. 1 is a diagram illustrating an implementation of a CT scanner system 100 for placing PCDs having a predetermined fourth-generation geometry in combination with a detector having a predetermined third-generation geometry in a CT scanner system. The diagram illustrates relative positions among an object 140 to be scanned, an X-ray source 101, an X-ray detector 103, and PCDs 150, in one exemplary embodiment. For the sake of simplicity, the diagram excludes other components and circuits that may be used in acquiring and processing data as well as reconstructing an image based upon the acquired data. In general, the PCDs 150 each output a photon count for each predetermined energy bin. In addition to the sparse PCDs 150 in the fourth-generation geometry, the implementation shown in FIG. 1 includes a detector, such as the detector 103, having a third-generation geometry in the CT scanner system 100. The detector elements in the detector 103 can be more densely placed along the detector surface than the PCDs 150.

In one implementation, the PCDs 150 are sparsely placed around the object 140 in a predetermined geometry such as a circle. For example, the PCDs 150 are fixedly placed on a circular component 110 in ae gantry of the CT scanner system 100. In one implementation, the PCDs 150 are fixedly placed on the circular component 110 at predetermined equidistant positions. In an alternative implementation, the PCDs 150 are fixedly placed on the circular component 110 at predetermined non-equidistant positions. The circular component 110 remains stationary with respect to the object 140 and does not rotate during data acquisition.

Both the X-ray source 101 and the detector 103 rotate around the object 140 while the PCDs 150 are stationary with respect to the object 140. In one implementation, the X-ray source 101 is mounted on a first rotating portion 120 of the gantry of the CT scanner system 100 so that the X-ray source 101 projects X-ray radiation with a predetermined source fan beam angle $\theta_A$ towards the object 140 while the X-ray source 101 rotates around the object 140 outside the sparsely-placed PCDs 150. Furthermore, detector 103 is mounted on a second rotating portion 130 having a third-generation geometry. The second rotating portion 130 mounts the detector 103 at a diametrically-opposed position from the X-ray source 101 across the object 140 and rotates outside the stationary circular component 110, on which the PCDs 150 are fixedly placed in a predetermined sparse manner.

In one implementation, the first and second rotating portions 120 and 130, respectively are integrally constructed as a single component to maintain a fixed angle (such as a 180-degree angle) between the X-ray source 101 and the detector 103 as they rotate about the object 140 with a different radius. In an optional implementation, the rotating portions 120 and 130 are separate components, but synchronously rotate to maintain the X-ray source 101 and the detector 103 in the fixedly opposed positions at 180-degrees across the object 140. Furthermore, the X-ray source 101 optionally travels a helical path as the object is moved in a predetermined direction that is perpendicular to the rotational plane of the rotating portion 120.

As the X-ray source 101 and the detector 103 rotate around the object 140, the PCDs 150 and the detector 103, respectively detect the transmitted X-ray radiation during data acquisition. The PCDs 150 intermittently detect with a predetermined detector fan beam angle $\theta_B$ the X-ray radiation that has been transmitted through the object 140 and each individually output a count value representing a number of photons, for each of predetermined energy bins. On the other hand, the detector elements in the detector 103 continuously detect the X-ray radiation that has been transmitted through the object 140 and output the detected signals as the detector 103 rotates. In one implementation, the detector 103 has densely placed energy-integrating detectors in predetermined channel and segment directions on the detector surface.

In one implementation, the X-ray source 101, the PCDs 150 and the detector 103 collectively form three predetermined circular paths that differ in radius. The PCDs 150 are sparsely placed along a first circular path around the object 140 while at least one X-ray source 101 rotates along a second circular path around the object 140. Further, the detector 103 travels along a third circular path. The above exemplary embodiment illustrates that the second circular path is the largest and outside the first and third circular paths around the object 140. Although not illustrated, an alternative embodiment optionally changes the relative relation of the first and second circular paths so that the second circular path for the X-ray source 101 is smaller and inside the first circular path of the sparsely placed PCDs 150 around the object 140. Furthermore, in another alternative embodiment, the X-ray source 101 also optionally travels on the same third circular path as the detector 103. Furthermore, the above alternative embodiments optionally provide a protective rear cover for each of the PCDs 150 that are irradiated from behind as the X-ray source 101 travels outside the first circular path of the sparsely placed PCDs 150.

There are other alternative embodiments for placing the PCDs 150 having a predetermined fourth-generation geometry in combination with the detector 103 having a predetermined third-generation geometry in the CT scanner system 100. The X-ray source 101 is optionally a single energy source in certain embodiments. By the same token, an additional alternative embodiment optionally includes the X-ray source 101, which is configured to or designed to perform a kV-switching function for emitting X-ray radiation at a predetermined high-level energy and at a predetermined low-level energy.

In general, the PCDs 150 are sparsely positioned along the circular component 110. Although the PCDs 150 acquire sparse view projection data, the acquired projection data is sufficient for at least dual-energy (DE) reconstruction with a sparse view reconstruction technique. In addition, the detector 103 also acquires another set of projection data, which is used to generally improve image quality. In the case that the detector 103 consists of energy-integrating detectors with anti-scatter grids, the projection data from the detector 103 is used to correct scatter on the projection data from the PCDs 150. In one implementation, the integrating detectors optionally need to be calibrated in view of X-ray transmission through the predetermined circular component 110 and some of the PCDs 150. In acquiring the projection data, a sampling on the source trajectory is optionally made sufficiently dense in order to try to enhance spatial resolution.

Figure 2:
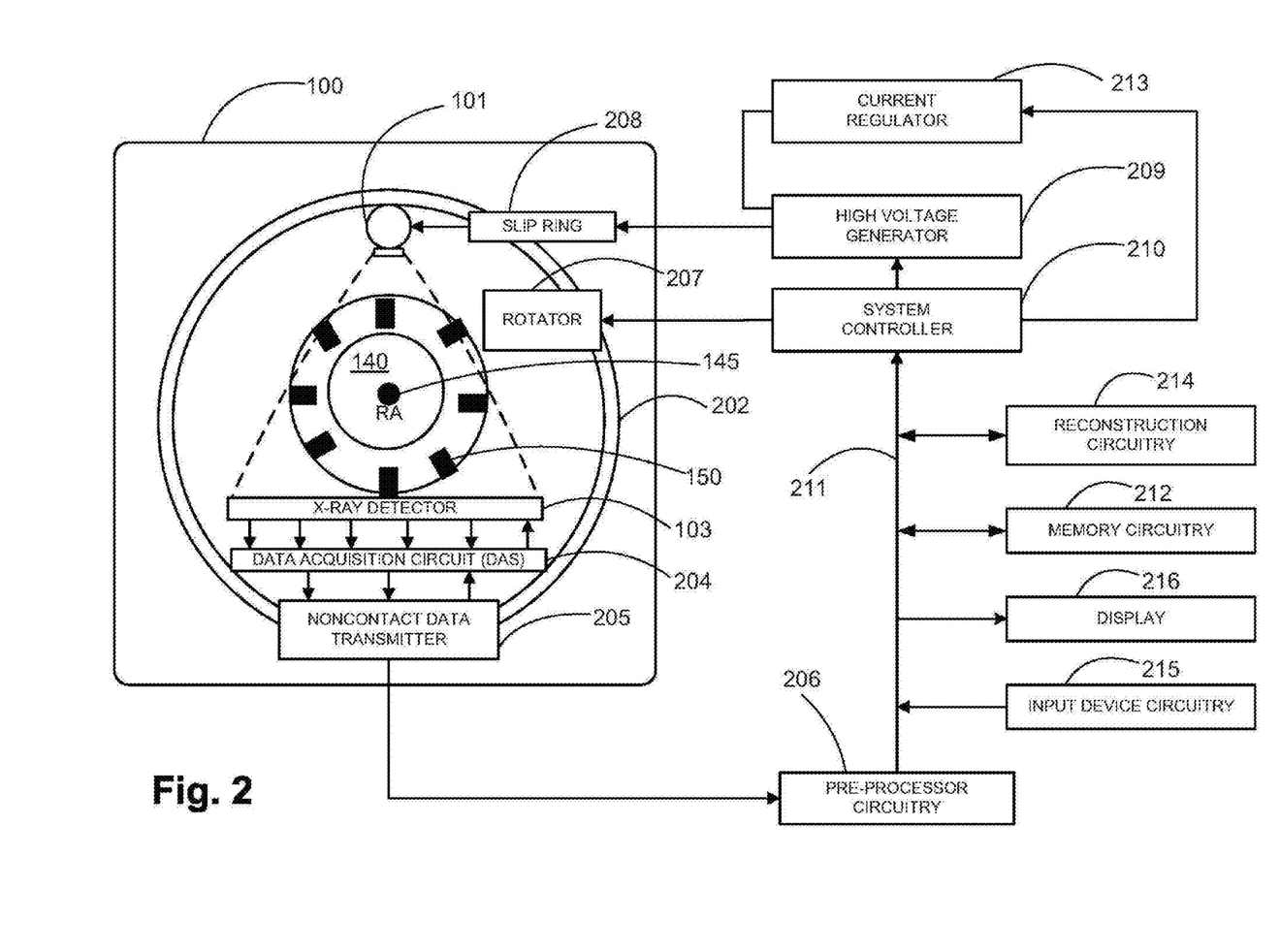
FIG. 2 illustrates an implementation of a CT system according to one embodiment.

FIG. 2 illustrates an implementation of the CT scanner system 100 of FIG. 1. As shown in FIG. 2, the CT scanner system 100 is illustrated from a side view and further includes an X-ray source 101, an annular frame 202, and a multi-row or two-dimensional array type of X-ray detector 103. The X-ray source 101 and X-ray detector 103 are diametrically mounted across an object 140 on the annular frame 202, which is rotatably supported around a rotation axis RA 145. A rotator 207 rotates the annular frame 202 at a high speed, such as 0.4 sec/rotation, while the object 140 is being moved along the axis RA 145 into or out of the illustrated page.

The CT scanner system 100 further includes a high voltage generator 209 that generates a tube voltage applied to the X-ray source 101 through a slip ring 208 so that the X-ray source 101 generates X-rays. The X-rays are emitted towards the object 140, whose cross-sectional area is represented by a circle. The X-ray detector 103 is located at an opposite side from the X-ray source 101 across the object 140 for detecting the emitted X-rays that have transmitted through the object 140. The X-ray detector 103 further includes individual detector elements or units. A current regulator 213 works in conjunction with the high voltage generator 209.

PCDs 150 are evenly spaced about the object 140 in a fixed circular pattern, such as circular component 110 illustrated in FIG. 1. The PCDs 150 each output a photon count for each pre-determined energy bin as the X-ray source 101 and X-ray detector 103 rotate about the object 140.

With continued reference to FIG. 2, the CT scanner system 100 further includes other devices for processing the detected signals from X-ray detector 103. A data acquisition circuit or a Data Acquisition System (DAS) 204 converts a signal output from the X-ray detector 103 for each channel into a voltage signal, amplifies the signal, and further converts the signal into a digital signal. The X-ray detector 103 and the DAS 204 are configured to handle a predetermined total number of projections per rotation (TPPR). Examples of TPPRs include, but are not limited to 900 TPPR, 900-1800 TPPR, and 900-3600 TPPR.

The above-described data is sent through pre-processor circuitry 206, which is housed in a console outside the CT scanner system 100 through a non-contact data transmitter 205. The pre-processor circuitry 206 includes hardware and software components to perform certain corrections, such as sensitivity correction on the raw data. Memory circuitry 212 includes one or more memory components, such as ROM, RAM, or various data storage components to store the resultant data, which is also called projection data at a stage immediately before reconstruction processing. The memory circuitry 212 is connected to a system controller 210 through a data/control bus 211, together with reconstruction circuitry 214, input device circuitry 215, and display 216. Reconstruction circuitry 214 can include hardware and software processing components working in conjunction with the circuitry. Each PCD 150 acquires sparse-view projection data from pre-processor circuitry 206 for reconstruction using a sparse-view reconstruction technique via reconstruction circuitry 214.

The detectors are rotated and/or fixed with respect to the object 140 among various generations of the CT scanner system 100. The above-described CT scanner system 100 is an example of a combined third-generation geometry and fourth-generation geometry system. In the third-generation system, the X-ray source 101 and the X-ray detector 103 are diametrically mounted on the annular frame 202 and are rotated around the object 140 as the annular frame 202 is rotated about the rotation axis RA 145. In the fourth-generation geometry system, the PCDs 150 are fixedly placed around the object 140 and the X-ray source 101 rotates around the object 140.

In an alternative embodiment, the CT scanner system 100 has multiple detectors arranged on the annular frame 202, which is supported by a C-arm and a stand.

Figure 3:
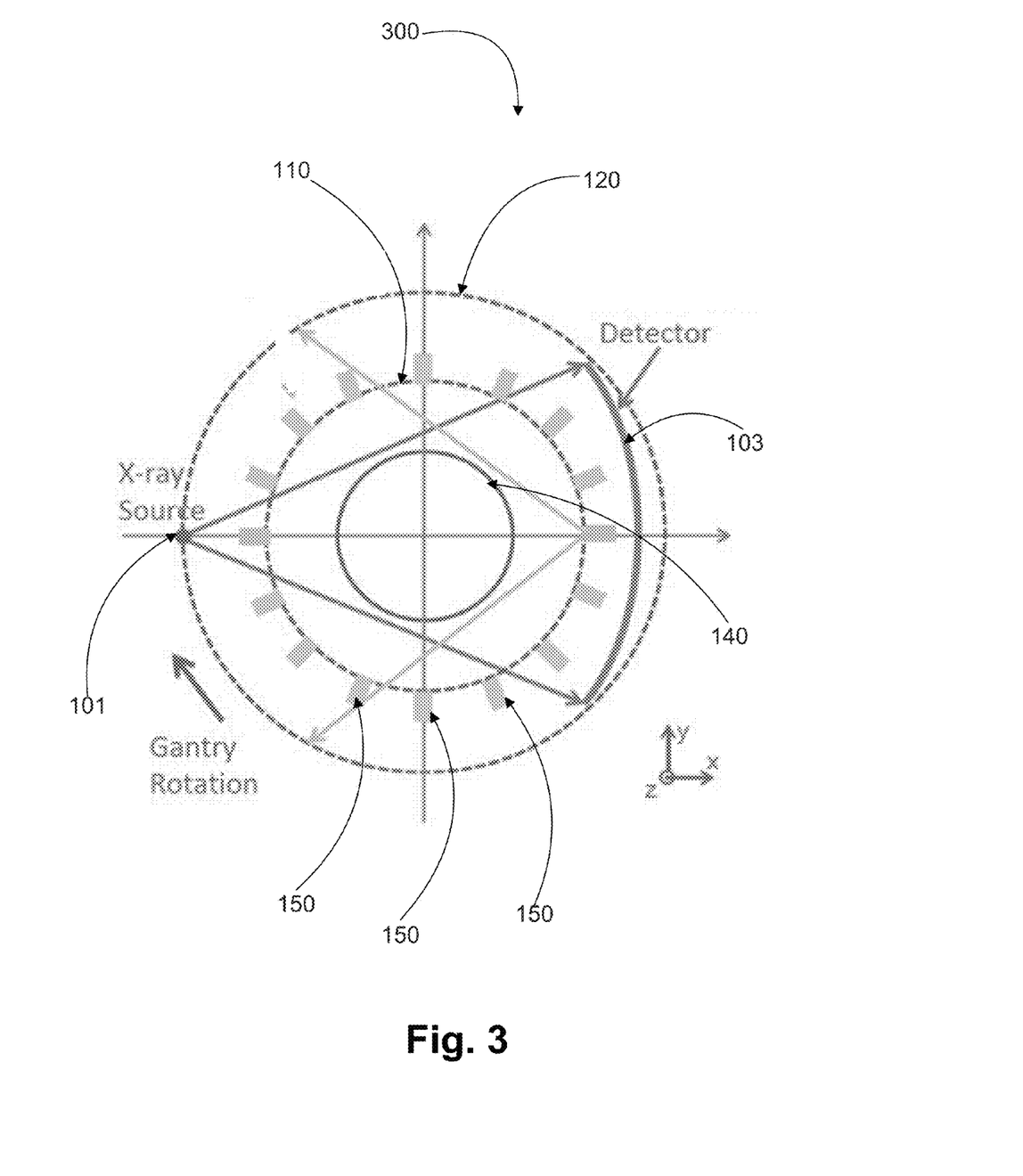
FIG. 3 illustrates a CT scanner system according to one embodiment.

FIG. 3 illustrates another CT scanner system 300 with X-ray source 101. The CT scanner system 300 includes PCDs 150 sparsely arranged in a pre-determined fourth-generation geometry around circular component 110. In one embodiment, circular component 110 remains stationary with respect to object 140 and does not rotate during the data acquisition. Detector 103 is arranged in a predetermined third-generation geometry around first rotating portion 120. X-ray source 101 orbits about the same first rotating portion 120 as detector 103, wherein X-ray source 101 and detector 103 are in fixed opposition with respect to each other within the first rotating portion 120. In general, each PCD 150 outputs a photon count for a corresponding predetermined energy bin. Each PCD 150 acquires sparse-view projection data for reconstruction using a sparse-view reconstruction technique. In the CT scanner system 300, circular component 110 resides within the first rotating portion 120.

Figure 4:
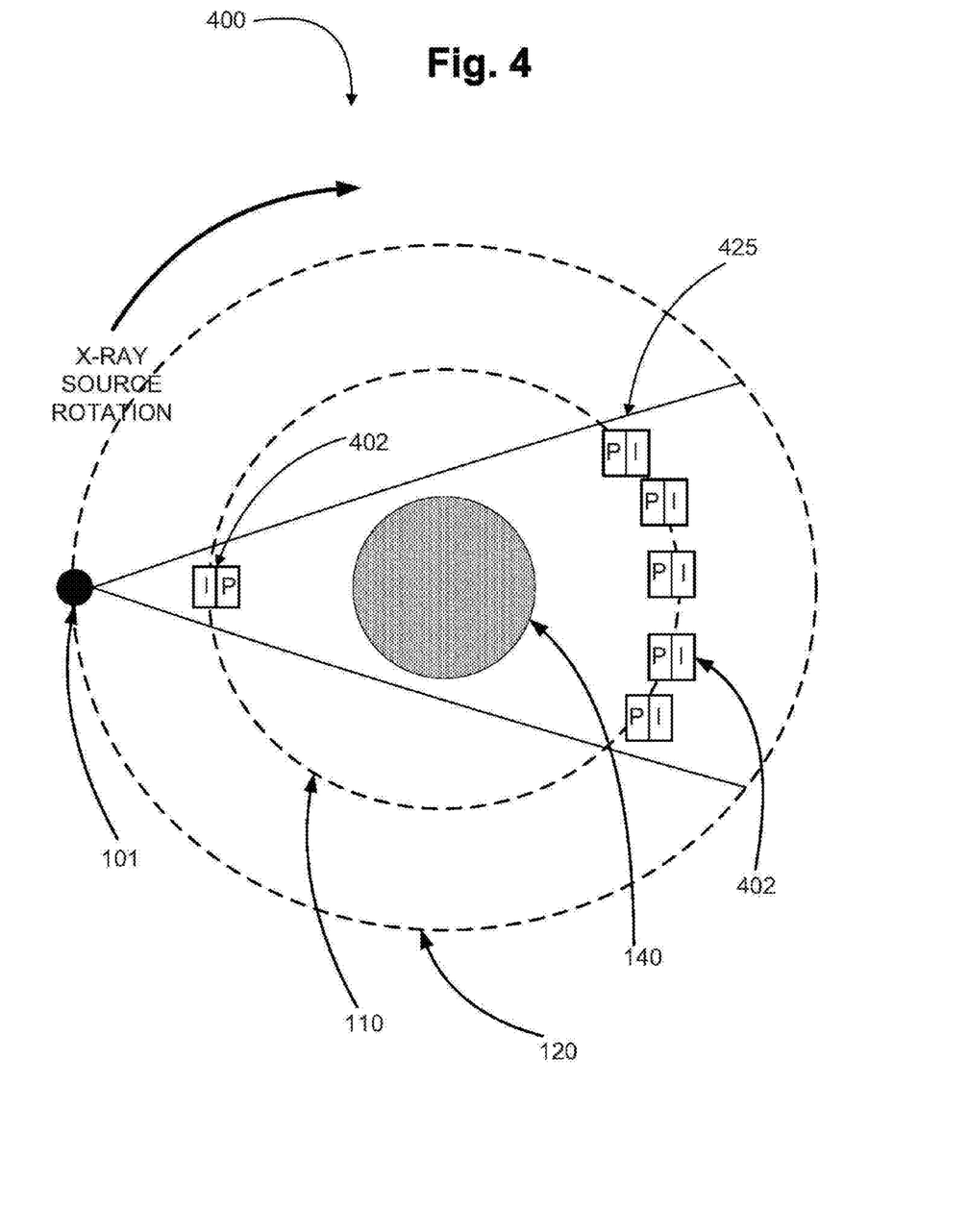
FIG. 4 illustrates a field-of-view of an X-ray source according to one embodiment.

FIG. 4 illustrates a field-of-view of an X-ray source of a CT scanner system 400. X-ray source 101 rotates about object 140 in first rotating portion 120. FIG. 4 also illustrates PCD assemblies 402 arranged in circular component 110, which are within a field-of-view 425 of X-ray source 101 at a certain instant of time. An actual CT scanner system may have more PCD assemblies 402 within a particular field-of-view 425. However, a smaller number of PCD assemblies 402 is illustrated in FIG. 4 for simplicity. Each PCD assembly 402 is illustrated as having an "I" portion and a "P" portion, wherein the "I" portion of each PCD assembly 402 directly faces the first rotating portion 120 of the X-ray source 101. The "P" represents a PCD and the "I" represents an interposer assembly module (IAM), which will be described in more detail with reference to FIG. 5.

A PCD assembly 402 is considered to be in a "near" field-of-view if it resides between the X-ray source 101 and the object 140, such as the single PCD assembly 402 located to the left side of the object 140 in FIG. 4. A PCD assembly 402 is considered to be in a "far" field-of-view if it resides on the distant side of the object 140 from the X-ray source 101, such as the five PCD assemblies 402 located to the right side of the object 140.

Figure 5:
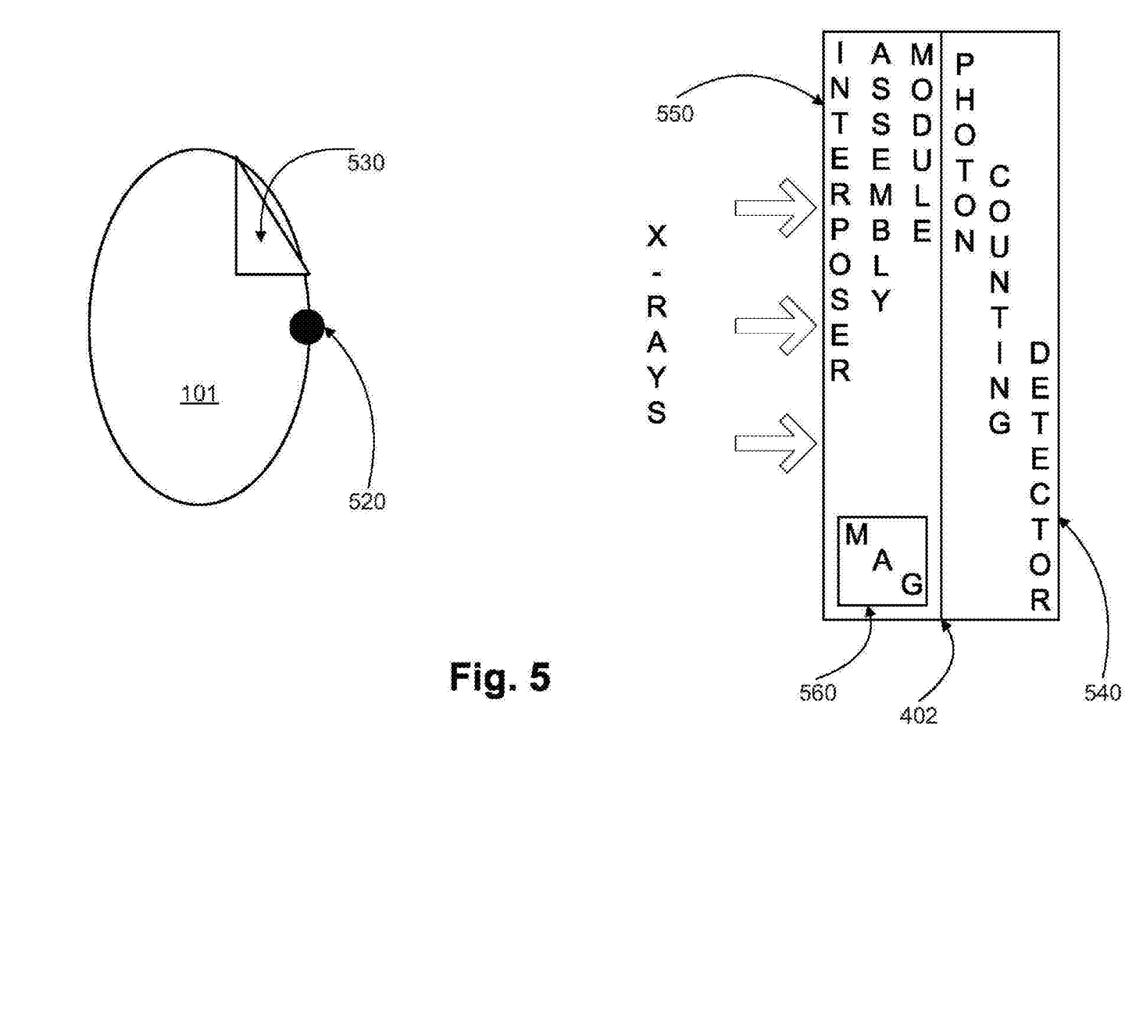
FIG. 5 is a block diagram of a side view of a photon counting detector (PCD) and an X-ray source according to one embodiment.

The right-hand portion of FIG. 5 is a block diagram of a side view of a PCD assembly 402 facing an anode focal point 520 of X-ray source 101 on the left-hand portion of FIG. 5. The front face of the PCD assembly 402 includes an IAM 550 in which e-mitted X-rays are received. The IAM 550 can include a sensor, such as a CdZnTe (CZT) sensor, a collimator, an application-specific integrated circuit (ASIC), and a board and associated traces. PCD 540 can also include a CZT sensor. The IAM 550 of FIG. 5 also illustrates a paramagnetic material, such as a magnet 560 at a lower portion of the IAM 550. The back face of PCD assembly 402 includes a PCD 540. When PCD assembly 402 comes within the near field-of-view of the X-ray source 101, the magnet 560 undergoes a magnetic attraction towards the X-ray source 101, due to a magnetic field gradient mechanism 530 located within or near to the X-ray source 101. With reference to FIG. 4, the single left PCD assembly 402 is located within the near field-of-view of the X-ray source 101.

The magnetic field gradient mechanism 530 can be fixed on the rotating gantry near the tube of the X-ray source 101. In one embodiment, the magnetic field gradient mechanism 530 is attached on the outside of a collimator assembly. The magnetic field gradient mechanism 530 can operate electromagnetically or with permanent magnets. The magnetic field is local and shielded; therefore, there are no effects to the X-ray tube or other components of the CT scanner system.

Figure 6:
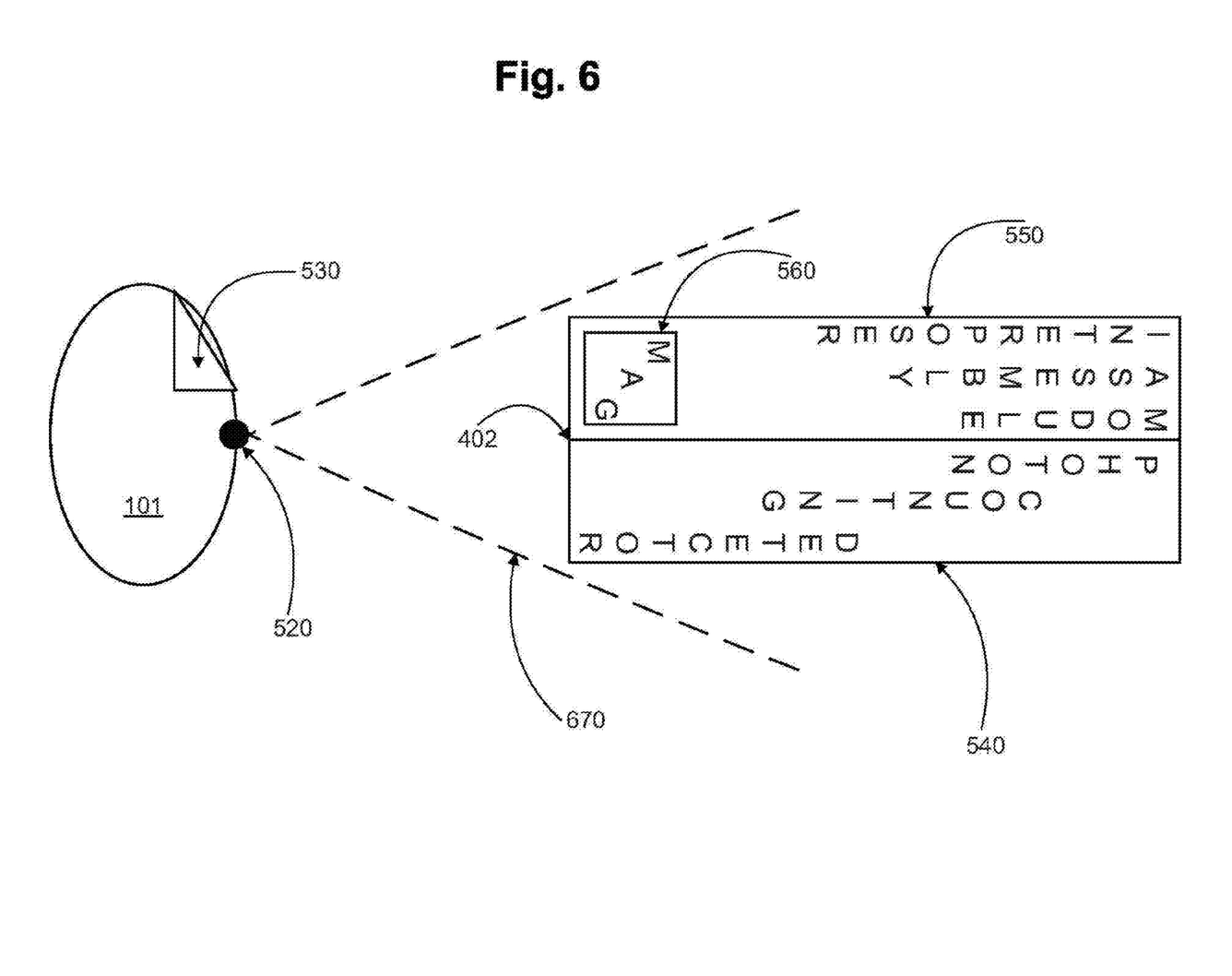
FIG. 6 is a block diagram illustrating a rotated PCD according to one embodiment.

FIG. 6 is a block diagram illustrating a rotated PCD assembly 402 having a magnet 560 within an IAM 550, and a PCD 540 on an opposite face of the PCD assembly 402. The PCD assembly 402 orbits within a near field-of-view 670 of an X-ray source 101 (illustrated from a side view), wherein X-rays are emitted from an anode focal point 520 of the X-ray source 101. The local magnetic field, caused by a magnetic field gradient mechanism 530 located within or near to the X-ray source 101 causes the PCD assembly 402 to rotate, as the magnet 560 is attracted to a stronger magnetic field of the magnetic field gradient mechanism 530, due to dipole interaction. The rotation mechanism will be described in more detail below with reference to FIG. 8. The rotation of the PCD assembly 402 allows the emitted X-rays from the X-ray source 101 to pass above and below the PCD assembly 402 without passing through the PCD assembly 402. When the X-ray source 101 continues its orbit past the near field-of-view with respect to PCD assembly 402, the PCD assembly 402 gradually returns to its upright position (see FIG. 5) since it is no longer within the local magnetic field.

Figure 7:
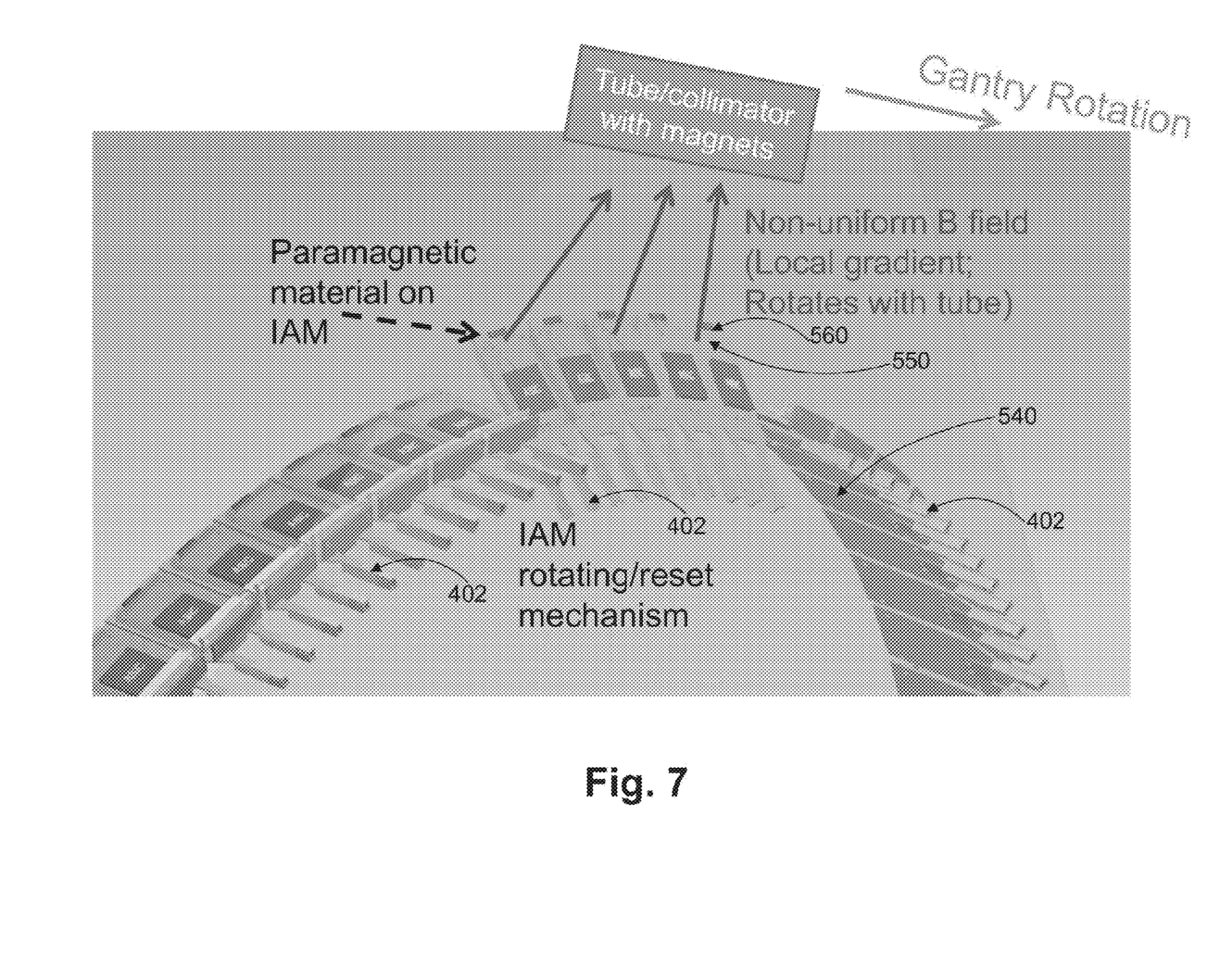
FIG. 7 illustrates a wide-angle view of a plurality of PCDs according to one embodiment.

FIG. 7 illustrates a wide-angle view of a plurality of PCD assemblies 402 arranged on a circular gantry component. In FIG. 7, emitted X-rays are coming from the top in the page from an X-ray source mounted on a gantry, wherein the emitted X-rays approach the PCD assemblies 402 at a near field-of-view. The X-ray source gantry rotates to the right in the page. Each of the PCD assemblies 402 contains a paramagnetic material 560, such as a magnet on the IAM 550 (upper face) of each PCD assembly 402. A PCD 540 is on the back face of the PCD assembly 402. Due to a magnetic field gradient mechanism located within or attached to the X-ray source, such as magnetic field gradient mechanism 530 illustrated in FIGS. 5 and 6, individual PCD assemblies 402 rotate their associated magnet 560 towards the X-ray source as it orbits past. The number of PCD assemblies 402 affected by the magnetic field mechanism at any point in time will vary, depending upon such factors as the magnetic strength, the distance of the X-ray source to the PCD assemblies 402, the rotational resistance of the PCD assemblies 402, and the orbital speed of the X-ray source. Other factors are disclosed by embodiments described herein.

FIG. 7 illustrates five PCD assemblies 402 rotated upwards, in response to a passing X-ray source (not illustrated) that includes a magnetic field gradient mechanism. However, the factors described above could cause fewer than or more than five PCD assemblies 402 rotating together. In addition, the rotation of the PCD assemblies 402 at the edges of the group of rotated PCD assemblies 402 will experience a weaker magnetic pull and therefore, might not rotate as far upward. The PCD assemblies 402 at the center of the local magnetic field will experience a maximum magnetic pull and therefore, likely rotate farther upward.

Figure 8A:
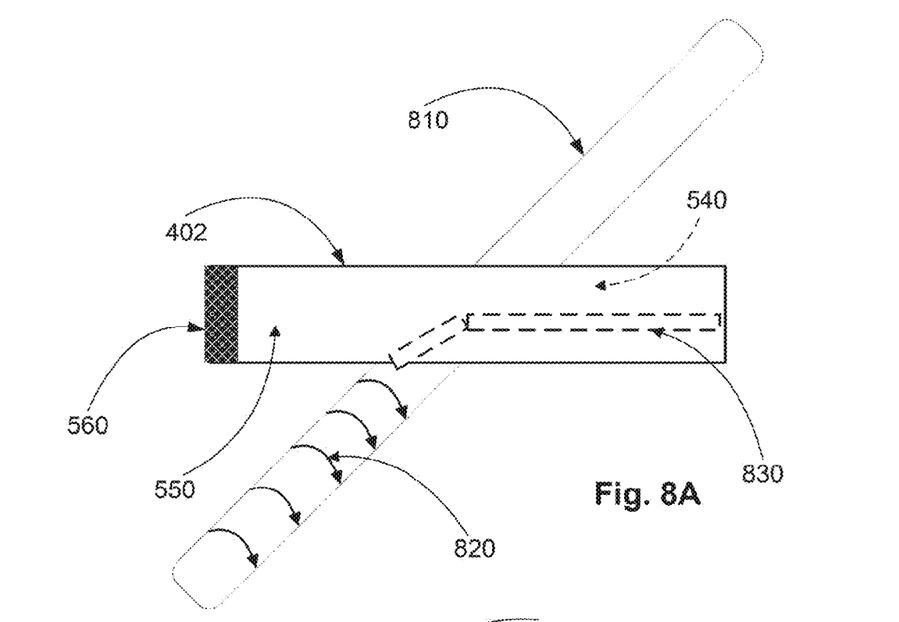
FIGS. 8A-8B illustrates a spring-loaded rotating mechanism according to one embodiment.

FIG. 8A illustrates a spring-loaded rotating mechanism by which a PCD assembly 402 rotates under the influence of a local magnetic field acting upon a magnet 560 located at one end of the PCD assembly 402. PCD assembly 402 includes an IAM 550 on a top side, which includes the magnet 560 at one end of the IAM. A PCD 540 is located on an underside of PCD assembly 402. The PCD assembly 402 is rotationally attached to a gantry circular component 810. A helical spring 820 is wrapped around a portion of the gantry circular component 810, and a spring linear extension 830 extends along an underside of the PCD assembly 402 away from the magnet 560 to form a spring-loaded rotating mechanism. FIG. 8A illustrates the PCD assembly 402 in a resting state in which there is no local magnetic field present. The spring linear extension 830 exerts a force against the PCD assembly 402 to keep the PCD assembly 402 in a horizontal position with respect to the gantry circular component 810. FIG. 8A is an illustration of the peripheral PCD assemblies 402 shown in FIG. 7 that are not within the influence of a local magnetic field.

Figure 8B:
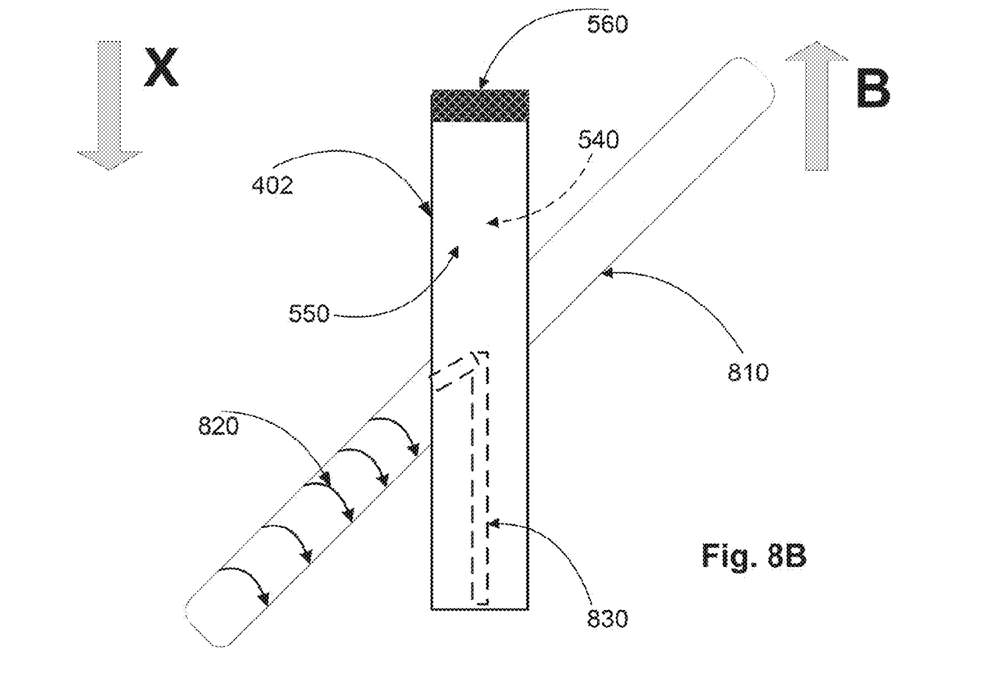

FIG. 8B illustrates a changed orientation of the PCD assembly 402 while under the influence of a local magnetic field B, such as a near-face orientation to an orbiting X-ray source (not illustrated), in which X-rays X are emanating in a downward direction of the page. A magnetic field gradient mechanism located within or near to the X-ray source causes a local magnetic field B upwards, which attracts the magnet 560 within the IAM 550 of the PCD assembly 402 and causes it to rotate upwards towards the magnetic field gradient mechanism.

In one embodiment, the IAM 550 is connected with supporting electronics via a flexible cable. This allows the PCD assembly 402 to actuate without affecting the electronics mounted on the gantry circular component 810 of the fixed, sparse PCD assemblies 402. The spring-loaded rotating mechanism responds to the local magnetic field B, and resets the PCD assembly 402 back to its original position via the spring-loaded rotating mechanism when the magnetic field gradient disappears, i.e. moves away.

The spring constant of the helical spring 820 and associated spring linear extension 830 is calculated according to variables of the CT scanner system, including, but not limited to the magnetic strength of the local magnetic field B and associated magnet 560, the distance of the X-ray source to the PCD assemblies 402, the rotational resistance of the PCD assemblies 402, and the orbital speed of the X-ray source. The spring-loaded rotating mechanism of the PCD assembly 402 utilizes a recoil force of a counter-wound spring at the rotating axis of the circular component 810 of the PCD assembly 402. The spring constant is designed to be low enough to allow the magnet 560 to rotate the PCD assembly 402 open and out of the path of the X-ray beam X, but still yield a high enough spring constant to assure the PCD assembly 402 is fully rotated back to its original alignment. When the PCD assembly 402 is no longer under the influence of the local magnetic field B, it returns to the resting state illustrated in FIG. 8A.

FIGS. 8A and 8B illustrate a helical spring 820 and associated spring linear extension 830. However, a leaf spring could also be used with the embodiments described herein. Other structural mechanisms that would allow a PCD assembly 402 to vertically rotate upon circular component 810 while under the influence of a local magnetic field B, as well as maintain a horizontal resting state upon the circular component 810 before and after the influence of the local magnetic field B are also contemplated by embodiments described herein.

Figure 9A:
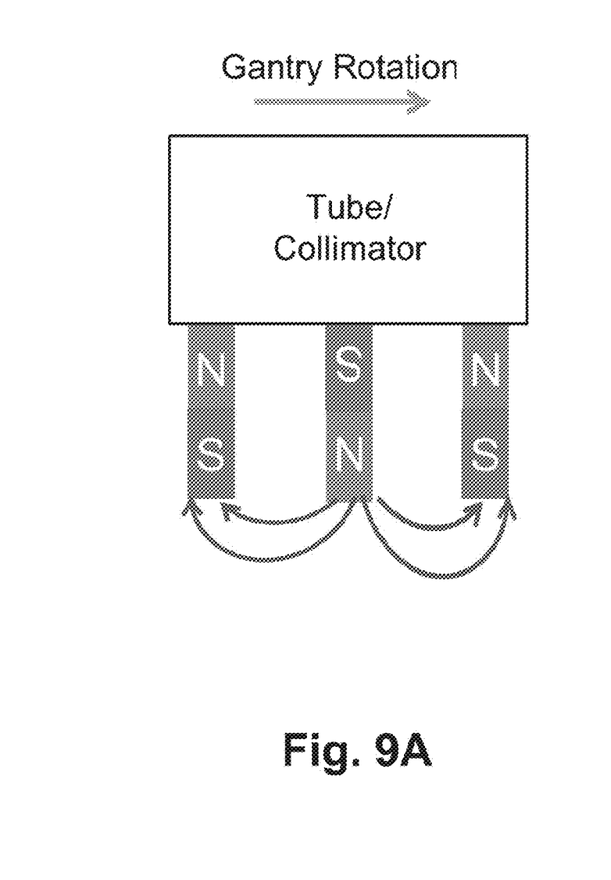
FIG. 9A is a block diagram of a combined X-ray source and magnetic field gradient mechanism according to one embodiment.

FIG. 9A illustrates a diagram for one embodiment of a combined X-ray source and magnetic field gradient. A gantry rotational orbit of the X-ray source causes magnetic fields between the mounted magnets with adjacent opposite poles. Embodiments include a magnetic field gradient that is combined in one device with the X-ray source attached to the X-ray source, or near to, but apart from, the X-ray source.

Figure 9B:
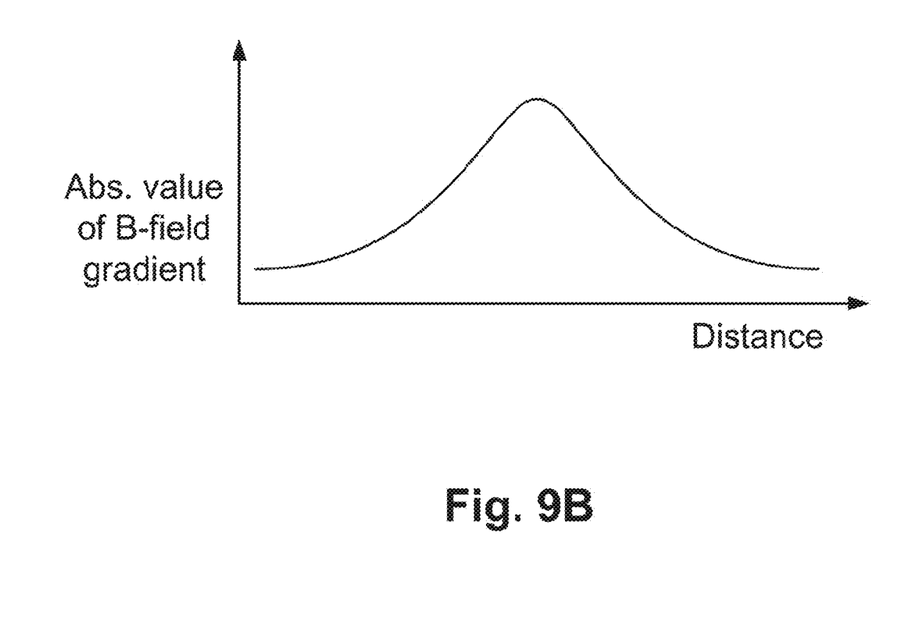
FIG. 9B is a graph illustrating the change in magnetic field gradient with distance across a PCD.

FIG. 9B is a graph illustrating the strength of a magnetic field gradient with respect to a distance of the magnetic field gradient from a PCD. It is desirable to create a magnetic field gradient that varies smoothly along the gantry rotational direction to enable smooth PCD actuations back and forth. With reference to the graph of FIG. 9B, the magnetic field gradient begins to increase when the IAM is at the side edge of a PCD. The magnetic field gradient continues to increase as the X-ray source orbits towards the center of the PCD, where it reaches a maximum strength at the center of the PCD. The magnetic field gradient begins to decrease as the X-ray source orbits away from the center of the PCD towards the opposite side edge of the PCD. The graph of FIG. 9B illustrates a general correspondence between a magnetic field strength and a distance from a PCD. However, the graphed correspondence could vary in terms of height, width, and maximum peak value, according to variables of the CT scanner system.

The CT scanner systems described herein overcome the disadvantages of conventional CT scanner systems, such as shadows, scattering, or beam spectral changes, which can complicate the spectral CT material decomposition and reconstruction. IAM shadows from the side of the X-ray source of conventional systems cause systematic photon starvation in fixed regions of the SFOV (scan field of view). X-ray registration between the third- and the fourth-generation geometries also requires close alignment of the IAM. A linear actuator and motion control sensor solution is difficult and expensive to obtain in this alignment. In addition, actuation of the IAMB from the front side of the X-ray source requires complex electronics and scan control to obtain synchronization between the third- and the fourth-generation geometries.

These disadvantages are obviated with the CT scanner systems described herein. Further, the amount of friction, noise, heating, and dust is minimized in the absence of mechanical contact between the rotating base and the stationary base. Also, a back-side shielding of the CZT sensor on the IAM is not required with embodiments described herein, since the near field-of-view PCD assemblies are rotated to be parallel with emitted X-rays and therefore, do not have X-rays passing through them.

The embodiments described herein provide a rotational mechanism for IAM actuation that ensures position repeatability. The described embodiments also account for two potential opposing IAMs present along a z-axis direction in a wide-cone configuration. In addition, there are no shadows in scanogram acquisition and parked-tube data acquisition from the X-ray-source side of the IAM. The IAMs in the field of view nearest the source will be rotated out of the field of view and therefore, no shadow will be observed by the IAMs in the field of view farthest away from the source.

While certain implementations have been described, these implementations have been presented by way of example only, and are not intended to limit the scope of the disclosure. The novel devices, systems, and methods described herein may be embodied in a variety of other forms. Furthermore, various omissions, substitutions, and changes in the form of the devices, systems, and methods described herein may be made without departing from the spirit of the disclosures. The accompanying claims are intended to cover such forms or modifications as would fall within the scope and spirit of the disclosures.

The invention claimed is:

1. A computed tomography (CT) scanner apparatus, comprising:
    an X-ray source mounted on a gantry of the CT scanner apparatus and configured to emit X-rays;
    at least one magnetic field gradient circuit, wherein the at least one magnetic field gradient circuit and the X-ray source rotate together;
    a CT detector mounted on the gantry in fixed orbital opposition to the X-ray source, the CT detector configured to detect the X-rays, wherein the CT detector and the X-ray source are configured to rotate along a first orbital path; and
    an array of fixed photon-counting detector (PCD) assemblies arranged on a fixed circular component in a ring inside the first orbital path, wherein each PCD assembly is fixed at a predetermined location to the circular component and is configured to rotatably actuate about the circular component from a first position to a second position to reduce blockage of emitted X-rays when the magnetic field gradient circuit rotates within a predetermined distance of the PCD assembly.

2. The CT scanner apparatus of claim 1, wherein each of the PCD assemblies includes an interposer assembly module (IAM).

3. The CT scanner apparatus of claim 2, wherein each of the IAMB directly faces the first orbital path of the X-ray source.

4. The CT scanner apparatus of claim 2, wherein each IAM includes a paramagnetic material located near an end of the corresponding PCD assembly.

5. The CT scanner apparatus of claim 4, wherein the paramagnetic material end of each PCD assembly is configured to rotate towards the magnetic field gradient circuit when the magnetic field gradient circuit orbits within the predetermined distance.

6. The CT scanner apparatus of claim 4, wherein the paramagnetic material comprises a magnet.

7. The CT scanner apparatus of claim 1, wherein each PCD assembly includes a spring mechanism to rotatably actuate the PCD assembly.

8. The CT scanner apparatus of claim 7, wherein the spring mechanism is configured to return each PCD assembly to the first position when the magnetic field gradient circuit is no longer within the predetermined distance.

* * * * *